(12) United States Patent
Kanno et al.

(10) Patent No.: US 7,964,546 B2
(45) Date of Patent: *Jun. 21, 2011

(54) ENDOSCOPE CLEANING METHOD AND WASHING MACHINE

(75) Inventors: Minoru Kanno, Sendai (JP); Takehisa Nakayama, Shinjuku-ku (JP)

(73) Assignee: Minoru Kanno, Sendai (JP)

( * ) Notice: Subject to any disclaimer, the term of this patent is extended or adjusted under 35 U.S.C. 154(b) by 285 days.

This patent is subject to a terminal disclaimer.

(21) Appl. No.: 12/087,608

(22) PCT Filed: Aug. 24, 2007

(86) PCT No.: PCT/JP2007/066428
§ 371 (c)(1),
(2), (4) Date: Jul. 10, 2008

(87) PCT Pub. No.: WO2008/059648
PCT Pub. Date: May 22, 2008

(65) Prior Publication Data
US 2009/0048133 A1  Feb. 19, 2009

(30) Foreign Application Priority Data
Nov. 16, 2006 (JP) ................. 2006-310803

(51) Int. Cl.
*C11D 17/00* (2006.01)
(52) U.S. Cl. ............ 510/161; 510/382; 134/42
(58) Field of Classification Search .......... None
See application file for complete search history.

(56) References Cited

U.S. PATENT DOCUMENTS

| 6,106,691 A | 8/2000 | Nakamura et al. |
| 2002/0017316 A1 | 2/2002 | Ochiai |
| 2004/0168933 A1 * | 9/2004 | Inoue ............ 205/746 |
| 2007/0009376 A1 | 1/2007 | Hamada et al. |

FOREIGN PATENT DOCUMENTS
EP  1 625 822 A1  2/2006
(Continued)

OTHER PUBLICATIONS

Supplementary European Search Report for European Application No. EP 07 80 6035 dated Aug. 10, 2010.

*Primary Examiner* — Necholus Ogden, Jr.
(74) *Attorney, Agent, or Firm* — Oliff & Berridge, PLC

(57) ABSTRACT

Provided are a method of cleaning an endoscope, a washing machine and a washing machine for endoscope, which can effectively clean an endoscope while preventing the endoscope from deterioration. The electrolytic cell 11 can produce from tap water acidic water with pH of 2 to 5 and the residual chlorine concentration of 50 to 300 ppm. A tank for acidic water 14 can store acidic water, in which part thereof can be fed to a tank of diluting acidic water 17 and the rest thereof can be fed to a feed section of concentrated water 20. A water feed section for dilution 16 can feed water for dilution to the tank of diluting acidic water 17. The tank of diluting acidic water 17 can add water for dilution from the water feed section for dilution 16 to part of the acidic water from the tank for acidic water 14 to adjust diluted acidic water to pH of 2.3 to 5.7 and the residual chlorine concentration of 10 to 60 ppm. The feed section of concentrated water 20 can feed the rest of acidic water fed from the tank for acidic water 14 through a channel connection port 20c to a channel port of an endoscope.

2 Claims, 4 Drawing Sheets

FOREIGN PATENT DOCUMENTS

| | | |
|---|---|---|
| JP | A 7-275811 | 10/1995 |
| JP | A 2000-126126 | 5/2000 |
| JP | A 2002-45334 | 2/2002 |
| JP | A 2002-52033 | 2/2002 |
| JP | A 2003-10116 | 1/2003 |
| JP | A 2003-145153 | 5/2003 |
| JP | A 2005-21250 | 1/2005 |
| WO | WO 2004/103168 A1 | 12/2004 |

* cited by examiner

ENDOSCOPE CLEANING METHOD AND WASHING MACHINE

TECHNICAL FIELD OF THE INVENTION

The present invention relates to a method of cleaning an endoscope, a washing machine and a washing machine for endoscope.

BACKGROUND ART

A channel of a flexible endoscope is a place, through which pass contaminants in organs, a body fluid such as mucus, blood and the like and pathogens and the like in a subject in the examination or in collecting a lesion tissue with an endoscope, and a place where definitive cleaning and sterilization are demanded. A long stainless steel wire equipped with a brush at tip has been generally heretofore inserted into an opening in the side at hand of each channel to manually brush for cleaning as a conventional method of cleaning the inside of a forceps channel, a suction channel and an air-supply and water-supply channel in an endoscope. There is also a method to use an automatic washing machine to drive a wire with a brush with a rubber roller instead of manual operation. (For example, see Patent Document 1).

Cleaning by a brush-equipped wire can realize a high cleaning effect when cleaned carefully, but it is required to that end to repeat an operation, in which the brush inserted into a channel is protruded through an opening at the tip of a channel to rub the brush with a finger in a cleaning liquid to remove contaminants remained and then pulled back to the opening in the side at hand to remove contaminants on the brush pulled out by similar operation, thus repeating insertion of the brush again to remove contaminants and then pullback. Accordingly, there has been a problem, in which this procedure takes time and an operator to perform the cleaning has a heavier burden. There has also been a problem, in which cleaning operation with a brush is only cursorily conducted, since preparation of a number of expensive endoscopes bears a heavy expense burden on the medical institution so that an endoscope used in a test is required to use for many occasions after cleaned and sterilized in as short a time as possible.

A method of using electrolytic water is practiced in cleaning an endoscope instead of cleaning with a brush in order to solve such problems. (See Patent Document 2, for example). In this conventional cleaning of an endoscope using electrolytic water, the electrolytic water with the same concentration of residual chlorine and water quality is used to clean and sterilize both the channel inside and the external surface of an endoscope.

Patent Document 1: Japanese Patent Publication 2003-10116
Patent Document 2: Japanese Patent Publication 2002-52033

PROBLEMS TO BE SOLVED BY THE INVENTION

When electrolytic water is used for cleaning and sterilization, sterilizing power and oxidative degradation ability against organic substances and the like depend on pH and a volume of residual chlorine to act. When pH is not varied, sterilizing power and decomposition ability therefore depend on the residual chlorine concentration in acidic water, a contact time with acidic water and a flow volume of acidic water to pass. In cleaning and sterilization, the higher the residual chlorine concentration is, the longer a contact time is and the more a flow volume to pass is, the higher the sterilizing effect and decomposition effect become, but accordingly a level of oxidative deterioration with an endoscope body becomes higher. In particular, a cladded resin to coat a fiber section of an endoscope is subject to oxidative degradation so that contact with acidic water with the high concentration of residual chlorine for a long period of time tends to cause whitening and stickiness of the surface.

In cleaning of an endoscope using conventional electrolytic water according to Patent Document 2, there has been a problem, in which electrolytic water with the same concentration of residual chlorine and water quality is used to clean and sterilize both the channel inside and external surface of an endoscope and acidic water with the high concentration of residual chlorine is contacted for a long period of time for cleaning to satisfy cleanliness in the channel inside, likely causing oxidative degradation of the member for the external surface of an endoscope and shortening a lifetime of the endoscope. There has been also a problem, in which when washed with acidic water with the relatively low concentration of residual chlorine for a short period of time, an external surface of the endoscope may be possibly cleaned and sterilized sufficiently because of easy removal of contaminants thereof, the channel inside is not sufficiently cleaned and sterilized, resulting in a risk with development of molds and the like by residual organic substances and infection among subjects with pathogens.

OBJECTS OF THE INVENTION

The present invention has been performed in concerning with such problems and has a purpose to provide a method of cleaning an endoscope, a washing machine and a washing machine for endoscope to give effective cleaning while preventing deterioration of an endoscope.

SUMMARY OF THE INVENTION

In order to accomplish the purpose described above, a method of cleaning an endoscope associated with the present invention comprises the steps of producing acidic water, adding water with pH higher than the above acidic water to part of the acidic water to produce diluted acidic water, contacting the above diluted acidic water with the external surface of the above endoscope to clean the external surface of the endoscope and feeding the rest of the above acidic water through a channel port of the above endoscope to the inside of the above channel to clean the inside of the above endoscope channel.

A method of cleaning an endoscope associated with the present invention preferably produces acidic water with pH of 2 to 5 and residual chlorine concentration of 50 to 300 ppm, adds water with pH equal to 6 or higher to part of the above acidic water to produce diluted acidic water with pH of 2.3 to 5.7 and residual chlorine concentration of 10 to 60 ppm, contacts the above diluted acidic water with the external surface of an endoscope to clean the external surface of the above endoscope and feeds the rest of the above acidic water through a channel port of the above endoscope to the inside of the above channel to clean the inside of the above endoscope channel.

The washing machine associated with the present invention comprises an electrolytic cell, a tank for acidic water, a water feed section for dilution, a tank of diluting acidic water, a cleaning vessel and a feed section of concentrated water, in which the above electrolytic cell is configured to produce acidic water, the above tank for acidic water is configured to store the above acidic water produced in the above electrolytic cell and feed part of the above acidic water stored to the above tank of diluting acidic water and the rest of the above acidic water to the above feed section of concentrated water, the above water feed section for dilution is configured to feed water for dilution to the above tank of diluting acidic water, the above tank of diluting acidic water is configured to mix and store part of the above acidic water fed from the tank for acidic water with water for dilution fed from the above water feed section for dilution and provided with a drain outlet to discharge the above diluted acidic water, the above cleaning vessel is configured to internally pool the above diluted acidic water discharged from the drain outlet of the above tank of diluting acidic water and the above feed section of concentrated water is configured to feed the rest of the above acidic water fed from the above tank for acidic water through the above channel connection port to the inside of the above cleaning vessel.

A washing machine for endoscope associated with the present invention comprises an electrolytic cell, a tank for acidic water, a water feed section for dilution, a tank of diluting acidic water and a feed section of concentrated water, in which the above electrolytic cell is configured to produce acidic water, the above tank for acidic water is configured to store the above acidic water produced in the above electrolytic cell and feed part of the above stored acidic water to the above tank of diluting acidic water and the rest of the above acidic water to the above feed section of concentrated water, the above water feed section for dilution is configured to feed water for dilution to the above tank of diluting acidic water, the above tank of diluting acidic water is provided to mix and store part of the above acidic water fed from the tank for acidic water with water for dilution fed from the above water feed section for dilution and provided with a drain outlet to discharge the above diluted acidic water and the above feed section of concentrated water is provided with a channel connection port connectable with a channel port of an endoscope and configured to feed the rest of the above acidic water fed from the above tank for acidic water through the above channel connection port.

The washing machine for endoscope associated with the present invention preferably comprises an electrolytic cell, a tank for acidic water, a water feed section for dilution, a tank of diluting acidic water and a feed section of concentrated water, in which the above electrolytic cell is configured to produce acidic water with pH of 2 to 5 and the residual chlorine concentration of 50 to 300 ppm from tap water, the above tank for acidic water is configured to store the above acidic water produced in the above electrolytic cell and feed part of the above stored acidic water to the above tank of diluting acidic water and the rest of the above acidic water to the above feed section of concentrated water, the above water feed section for dilution is configured to feed water for dilution with pH equal to 6 or higher to the above tank of diluting acidic water, the above tank of diluting acidic water is configured to add water for dilution fed from the above water feed section for dilution to part of the above acidic water fed from the above tank for acidic water, adjusting diluted acidic water to pH of 2.3 to 5.7 and the residual chlorine concentration of 10 to 60 ppm and provided with a drain outlet to discharge the above diluted acidic water and the above feed section of concentrated water is provided with a channel connection port connectable with the channel port of an endoscope and configured to feed the rest of the above acidic water fed from the above tank for acidic water through the above channel connection port.

In the present invention, acidic water with the high concentration of residual chlorine is separately used from diluted acidic water after dilution of the acidic water to prevent the equipment from deterioration and efficiently clean it.

In a method of cleaning an endoscope and a washing machine for endoscope associated with the present invention, acidic water can be fed through the channel port of an endoscope into the channel inside to clean the inside of an endoscope channel. Diluted acidic water after dilution of the acidic water can also contact the external surface of the endoscope to clean the external surface of the endoscope. Acidic water with the high concentration of residual chlorine is used to clean the inside of the endoscope channel, enabling to effectively remove contaminants in the channel inside within a short period of time. Diluted acidic water is also used to clean the external surface of the endoscope, enabling to prevent the external surface of an endoscope from oxidative degradation and to remove contaminants on the external surface of the endoscope. The method of cleaning an endoscope associated with the present invention can thus clean the endoscope efficiently and effectively within a short period of time while preventing the endoscope from deterioration.

When acidic water with pH of 2 to 5 and the residual chlorine concentration of 50 to 300 ppm is separately used from diluted acidic water with pH of 2.3 to 5.7 and the residual chlorine concentration of 10 to 60 ppm in the method of cleaning an endoscope and the washing machine for endoscope associated with the present invention, the acidic water with pH of 2 to 5 and the residual chlorine concentration of 50 to 300 ppm can be fed through the channel port of an endoscope into the channel inside to clean the inside of the endoscope channel. Diluted acidic water with pH of 2.3 to 5.7 and the residual chlorine concentration of 10 to 60 ppm contacts the external surface of an endoscope enabling to clean the external surface of the endoscope. The acidic water with the high concentration of residual chlorine is used to clean the inside of an endoscope channel enabling to effectively clean contaminants in the channel inside within a short period of time. The diluted acidic water, in which the acidic water is diluted in two- to five-fold is used to clean the external surface of an endoscope enabling to prevent the external surface of the endoscope from oxidative degradation and to remove contaminants on the external surface of the endoscope. The method of cleaning an endoscope associated with the present invention can thus clean the endoscope efficiently and effectively within a short period of time while preventing the endoscope from deterioration.

A washing machine associated with the present invention can be used as a machine of washing table wares, vegetables and the like in a sink, a machine of washing marine products at fish market and a machine of washing various other products in addition to a washing machine for endoscope.

In the present invention, acidic water is preferably 80 to 150 ppm with the residual chlorine concentration and diluted acidic water is preferably 2.5 to 4.5 with pH and 20 to 50 ppm with the residual chlorine concentration. In these cases, particularly excellent cleaning effect is obtained. Diluted acidic water may be pooled in a cleaning vessel, in which an endoscope is immersed or diluted acidic water may be sprayed onto the endoscope in order to contact the diluted acidic water with the external surface of an endoscope. The acidic water may be produced in a diaphragm type electrolytic cell or non-diaphragm type electrolytic cell.

The present invention can provide a method of cleaning an endoscope, a washing machine and a washing machine for endoscope to effectively clean an endoscope while preventing it from deterioration.

EXPLANATION OF LETTERS AND NUMERALS

Figure 1:
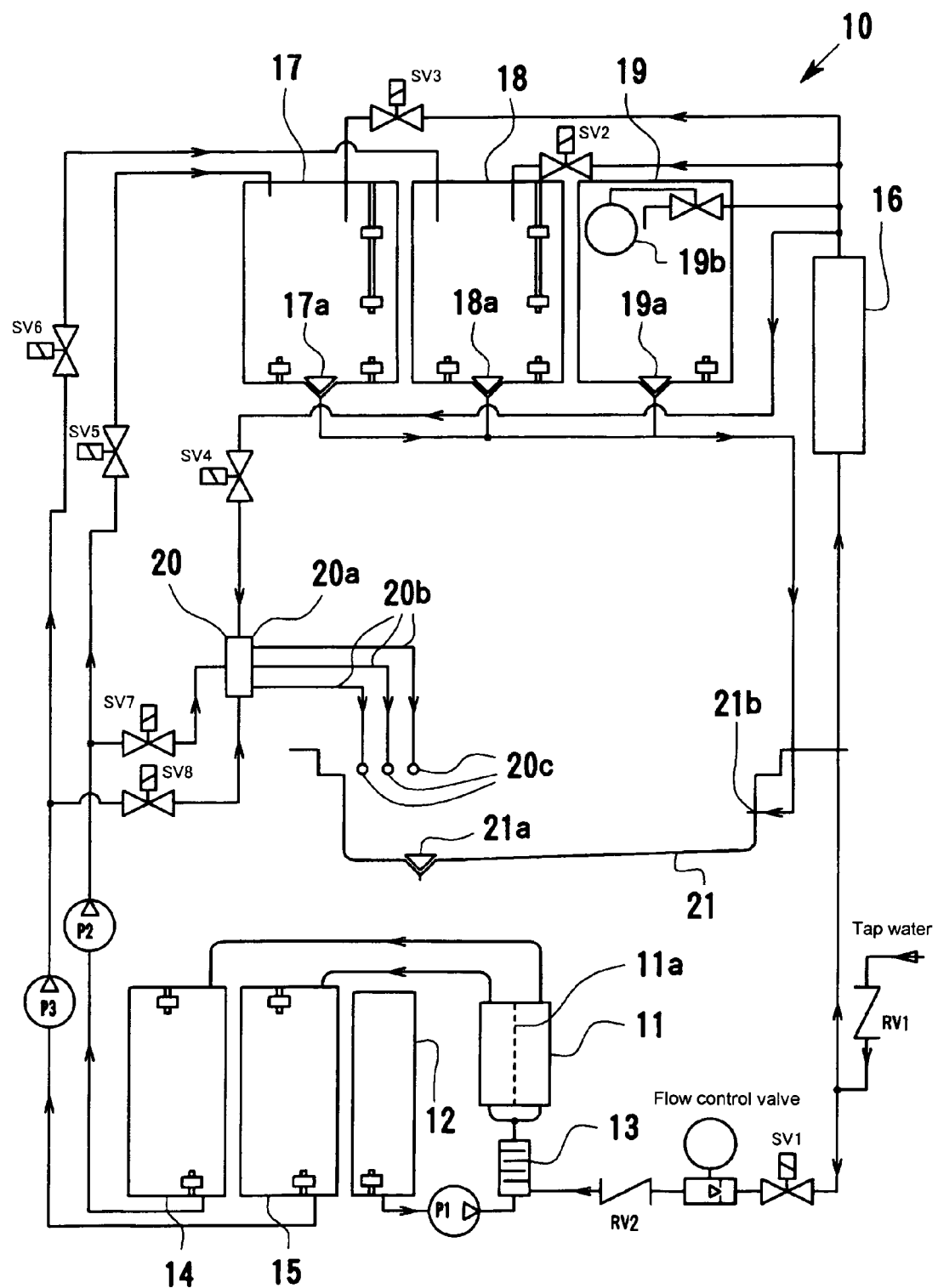
FIG. 1 is a block diagram illustrating a method of cleaning an endoscope and a washing machine for endoscope in an embodiment of the present invention.

10: Washing machine for endoscope
11: Electrolytic cell
12: Electrolyte tank
13: Mixing section
14: Tank for acidic water
15: Tank for alkaline water
16: Water feed section for dilution
17: Tank of diluting acidic water
18: Tank of diluting alkaline water
19: Tank for tap water
20: Feed section of concentrated water
21: Cleaning vessel

DETAILED DISCLOSURE OF THE PREFERRED EMBODIMENT

An embodiment of the present invention is described below based on the drawings.

FIGS. 1 to 4 illustrate a method of cleaning an endoscope and a washing machine for endoscope in the embodiments of the present invention.

As shown in FIG. 1, a washing machine for endoscope 10 comprises an electrolytic cell 11, an electrolyte tank 12, a mixing section 13, a tank for acidic water 14, a tank for alkaline water 15, a water feed section for dilution 16, a tank of diluting acidic water 17, a tank of diluting alkaline water 18, a tank for tap water 19, a feed section of concentrated water 20 and a cleaning vessel 21.

The electrolytic cell 11 is internally provided with a diaphragm 11a and composed of a diaphragm type electrolytic cell with two compartments, which is divided into an anode chamber and a cathode chamber separated by a diaphragm 11a. The electrolytic cell 11 can electrolyze tap water mixed with an electrolyte solution at a given ratio, to which an electrolyte such as a common salt and the like is added to produce acidic water in the anode chamber and alkaline water in the cathode chamber. The electrolytic cell 11 is configured to produce acidic water with pH of 2 to 5 and the residual chlorine concentration of 50 to 300 ppm. The electrolytic cell 11 can also produce alkaline water with pH of 11.5 to 12.5.

The electrolyte tank 12 stores an electrolyte solution and is connected with a mixing section 13 through an electrolyte conveying pump P1. The mixing section 13 allows inflow of tap water passed through a check valve RV1, an electromagnetic valve SV1, a flow control valve and a check valve RV2. The mixing section 13 is connected with the electrolytic cell 11 to mix an electrolyte solution with tap water in a given ratio to feed to the electrolytic cell 11.

The tank for acidic water 14 is connected with the electrolytic cell 11 and can store acidic water produced in the electrolytic cell 11. The tank for acidic water 14 is connected with the tank of diluting acidic water 17 through a pump P2 and an electromagnetic valve SV5, branched after a pump P2 and connected with the feed section of concentrated water 20 through an electromagnetic valve SV7. The tank for acidic water 14 is configured to feed part of the stored acidic water to the tank of diluting acidic water and the rest of the acidic water to the feed section of concentrated water 20.

The tank for alkaline water 15 is connected with the electrolytic cell 11 and can store alkaline water produced in the electrolytic cell 11. The tank for alkaline water 15 is connected with the tank of diluting alkaline water 18 through a pump P3 and an electromagnetic valve SV6, branched after a pump P3 and connected with the feed section of concentrated water 20 through an electromagnetic valve SV8. The tank for alkaline water 15 is configured to feed part of the stored alkaline water to the tank of diluting alkaline water 18 and the rest of the alkaline water to the feed section of concentrated water 20.

The water feed section for dilution 16 is provided with a filter. The water feed section for dilution 16 is connected between a check valve RV1 and an electromagnetic valve SV1 to produce water for dilution after filtering fine contaminants and microorganisms in tap water. The water feed section for dilution 16 is connected with the tank of diluting acidic water 17 through an electromagnetic valve SV3, with the tank of diluting alkaline water 18 through an electromagnetic valve SV2, with a tank for tap water 19 and with a feed section of concentrated water 20 through an electromagnetic valve SV4, enabling to feed water for dilution to the tank of diluting acidic water 17, the tank of diluting alkaline water 18, the tank for tap water 19 and the feed section of concentrated water 20.

The tank of diluting acidic water 17 is provided with a drain outlet 17a at the lower part. The tank of diluting acidic water 17 is configured to add water for dilution fed from the water feed section for dilution 16 to part of the acidic water fed from the tank for acidic water 14, enabling to adjust the diluted acidic water to pH of 2.3 to 5.7 and the residual chlorine concentration of 10 to 60 ppm. The tank of diluting acidic water 17 is also configured to discharge diluted acidic water from the drain outlet 17a.

The tank of diluting alkaline water 18 is provided with a drain outlet 18a at the lower part. The tank of diluting alkaline water 18 is configured to add water for dilution fed from the water feed section for dilution 16 to part of alkaline water fed from the tank for alkaline water 15, enabling to adjust diluted alkaline water to pH of 11 to 11.8. The tank of diluting alkaline water 18 is also configured to discharge diluted alkaline water from a drain outlet 18a.

The tank for tap water 19 is provided with a drain outlet 19a at the lower part and with a ball tap 19b in the upper part. The tank for tap water 19 is configured to pass water for dilution fed from the water feed section for dilution 16 through the ball tap 19b to store. The tank for tap water 19 is also configured to discharge water for dilution from the drain outlet 19a.

The feed section of concentrated water 20 is provided with a distributor 20a and three couplings for channel cleaning water 20b connected with the distributor 20a. The distributor 20a is configured to distribute and feed either one of acidic water from the tank for acidic water 14, alkaline water from the tank for alkaline water 15 or water for dilution from the water feed section for dilution 16 to each of couplings for channel cleaning water 20b. Each of couplings for channel cleaning water 20b is provided with channel connection ports 20c at each tip connectable with a forceps channel port, a suction channel port and an air-supply and water-supply channel port of an endoscope. The tank for acidic water 14 is thus configured to feed either one of acidic water from the tank for acidic water 14, alkaline water from the tank for alkaline water 15 or water for dilution from the water feed section for dilution 16 through each of channel connection ports 20c.

The cleaning vessel 21 is provided with a drain valve 21a at the lower part and an injection port 21b at the side enabling to internally accommodate an endoscope at a given location. The cleaning vessel 21 is configured to connect the injection port 21b with the drain outlet 17a of the tank of diluting acidic water 17, with the drain outlet 18a of the tank of diluting alkaline water 18 and with the drain outlet 19a of the tank for tap water 19 and flow diluted acidic water, diluted alkaline water and water for dilution in the inside through the injection port 21b to store. The cleaning vessel 21 is configured to discharge diluted acidic water, diluted alkaline water or water for dilution stored in the inside from the drain valve 21a.

A method of cleaning an endoscope in an embodiment of the present invention is a method to practice with a washing machine for endoscope 10 in the embodiment of the present invention. When a main cock for tap water is opened, tap water at first passes through a check valve RV1 to branch into two, in which one reaches an electromagnetic valve SV1 for controlling water supplied to the electrolytic cell 11 and the other passes through the water feed section for dilution 16 and branch into passing through the ball tap 19b to be stored in the tank for tap water 19 and reaching the electromagnetic valves SV2 and SV3 for controlling water to flow in each of the tank of diluting acidic water 17 and the tank of diluting alkaline water 18 and the electromagnetic valve SV4 for controlling water to feed to the distributor 20a.

When a power source SW of the washing machine for endoscope 10 is next turned on, the electromagnetic valve SV1 is opened to feed tap water, which passes through the flow control valve and the check valve RV2 to reach the mixing section 13. At the same time, an electrolyte conveying pump P1 starts running to feed a given amount of an electrolyte solution into the mixing section 13. Tap water is mixed with the electrolyte solution at a given ratio in the mixing section 13 to be electrolyzed in the electrolytic cell 11 to produce acidic water and alkaline water to be pooled in the tank for acidic water 14 and the tank for alkaline water 15, respectively. The produced acidic water has pH of 2 to 5 and residual chlorine concentration of 50 to 300 ppm and the produced alkaline water contains no or little residual chlorine. The electromagnetic valves SV2 and SV3 are opened to flow water for dilution into the tank of diluting acidic water 17 and the tank of diluting alkaline water 18 and the electromagnetic valves SV2 and SV3 are closed when a specified volume of water is reached.

When acidic water and alkaline water are pooled in a given amount in the tank for acidic water 14 and the tank for alkaline water 15, respectively, the conveying pumps P2 and P3 start running. At the same time, the electromagnetic valves SV5 and SV6 are opened to feed acidic water and alkaline water to the tank of diluting acidic water 17 and the tank of diluting alkaline water 18, respectively, to flow into water for dilution pooled in advance. When a given amount is reached, the electromagnetic valves SV5 and SV6 are closed and the pumps P2 and P3 are turned off. A required amount of diluted acidic water with a residual chlorine concentration for cleaning of an external surface and diluted alkaline water is thus pooled in the tank of diluting acid water 17 and the tank of diluting alkaline water 18. The diluted acidic water has pH of 2.3 to 5.7 and residual chlorine concentration of 10 to 60 ppm.

When acidic water in the tank for acidic water 14 or alkaline water in the tank for alkaline water 15 is lowered to a given water level in the way to feed acidic water and alkaline water to the tank of diluting acidic water 17 and the tank of diluting alkaline water 18, respectively, the corresponding pumps P2 and P3 are turned off, but tuned on to feed the water again when the acidic water or alkaline water is pooled in a given volume. Electrolytic production of acidic water and alkaline water in the electrolytic cell 11 is automatically stopped when the tank for acidic water 14 and the tank for alkaline water 15 are filled to full capacity.

An endoscope is next placed in a given location of the cleaning vessel 21 to connect the channel connection ports 20c of the couplings for channel cleaning water with each channel port of the endoscope. When a switch to start cleaning is turned on, a drain valve 21a of the cleaning vessel 21 is closed and a drain outlet 18a of the tank of diluting alkaline valve 18 is opened to flow diluted alkaline water, in which concentration is adjusted as water of cleaning the external surface of an endoscope into the cleaning vessel 21 to clean the external surface. At the same time, the pump P3 starts running and an electromagnetic valve SV8 is opened to feed concentrated alkaline water at pH of 11.5 to 12.5 through the distributor 20a and the couplings for channel cleaning water 20b to each of the inside of the endoscope channel to clean the channel inside. The higher the concentration of the hydroxyl ion is, the higher the decomposition and cleaning power of alkaline water is with proteins and fats, thereby effectively removing contaminants such as proteins, fats and the like in each channel. Contaminants are thus removed in advance before cleaning with acidic water to enhance a cleaning and sterilizing effect. Alkaline water, which passes to clean the channel inside is discharged into the cleaning vessel 21 and diluted with diluted alkaline water.

When a set time for cleaning with alkaline water elapses, the drain valve 21a of the cleaning vessel 21 is opened to discharge diluted alkaline water in the cleaning vessel 21. At the same time, the pump P3 is turned off and an electromagnetic valve SV8 is closed to terminate feeding alkaline water into the channel inside. When draining diluted alkaline water is completed, the drain outlet 19a of the tank for tap water 19 is opened to feed water for dilution to the cleaning vessel 21. At the same time, an electromagnetic valve SV4 is opened to feed water for dilution through the distributor 20a and the couplings for channel cleaning water 20b to the channel inside. This allows to flush out alkaline water remained on the external surface and the channel inside of an endoscope and decomposed residues of contaminants formed by the reaction with alkaline water. When a set time for rinsing and cleaning with water elapses, water for dilution in the cleaning vessel 21 is discharged similarly as cleaning with alkaline water and the electromagnetic valve SV4 is closed to terminate feeding water into the channel inside.

When draining of water from the cleaning vessel 21 is completed, similarly as washing with alkaline water, diluted acidic water, of which concentration is adjusted as water of cleaning the external surface of an endoscope and pH and residual chlorine concentration are 2.3 to 5.7 and 10 to 60 ppm, respectively, is fed from the tank of diluting acidic water 17 to the cleaning vessel 21 to contact the diluted acidic water with the external surface to clean it. At the same time, the pump P2 starts running and an electromagnetic valve SV7 is opened to feed concentrated acidic water with pH of 2 to 5 and the residual chlorine concentration of 50 to 300 ppm into the channel inside to clean it. Thereby acidic water with the high concentration of residual chlorine cleans the inside of an endoscope channel, enabling to effectively clean contaminants in the channel inside within a short period of time. Diluted acidic water, obtained by the dilution in a range of twofold to fivefold, is used to clean the external surface of an endoscope, enabling to prevent the external surface of the endoscope from oxidative degradation and remove contaminants of the external surface of the endoscope. Cleaning can thus be performed efficiently and effectively within a short period of time while preventing the endoscope from deterioration.

Acidic water which passed through the channel inside is discharged into the cleaning vessel 21. At this time, a volume of acidic water which passed through the inside of thin channel ranges in a level of one fifth to one fifteenth as low as a volume of diluted acidic water in the cleaning vessel 21 and residual chlorine is consumed by the reaction with contaminants when passing the channel, thus resulting in no increase in a volume of residual chlorine in the cleaning vessel and no danger of damaging the external surface. When a set time for cleaning with acidic water elapses, diluted acidic water in the cleaning vessel 21 is discharged similarly as cleaning with alkaline water to terminate feeding acidic water into the channel inside. When draining of water from the cleaning vessel is completed, a process of rinsing and washing again with water for dilution in the tank for tap water 19 is followed to complete cleaning and sterilizing of an endoscope.

Acidic water with the high concentration of residual chlorine and low pH and alkaline water with high pH are dangerous when directly contacting a human body. Alkaline water with pH surpassing 12 is in particular dangerous. Concentrated acidic water and concentrated alkaline water are consequently used only in cleaning and sterilizing the inside of each endoscope channel and diluted acidic water and diluted alkaline water are fed to the cleaning vessel 21, which is likely to have a direct contact during cleaning.

A pump may be used as needed to feed water from the tank of diluting acidic water 17, the tank of diluting alkaline water 18 and the tank for tap water 19. The tank for tap water 19 may be provided with electrodes. In this case, electric charges can be generated between the electrodes to generate hypochlorous acid, the hydochloride ion and the like from chlorine and chloride ion contained in water to prevent microorganisms in the tank for tap water 19 from reproduction. The method of cleaning an endoscope and the washing machine for endoscope 10 in the embodiment of the present invention is not limited to cleaning of the endoscope, but useful to effective cleaning of a medical equipment, a food processing equipment and the like with a space or passage, which is unreachable directly by hand from the outside.

The electrolytic cell 11 may be composed of a three compartments type cell with a middle chamber separated from an anode electrolysis chamber and from a cathode electrolysis chamber by two sheets of diaphragm. In this case, water, to which an electrolyte is not in particular added such as tap water and the like is routed to the anode electrolysis chamber, an aqueous electrolyte solution such as a brine at a nearly saturated concentration fills up the middle chamber to electrolyze, anions such as a chloride ion are migrated from the middle chamber to the anode electrolysis chamber and cations such as a sodium ion are migrated into the cathode electrolysis chamber, enabling to produce acidic water in the anode electrolysis chamber and alkaline water in the cathode electrolysis chamber while maintaining pH of the middle chamber to be nearly neutral. It may be composed of an electrolytic cell, in which one chamber separated by a diaphragm 11a is filled up with a concentrated aqueous electrolyte solution, and which, by passing tap water and the like through the other chamber and by switching the electrode polarity, converts passing tap water and the like to acidic electrolytic water or alkaline electrolytic water. In case of the electrolytic cell 11 with a diaphragm, when acidic water with low pH and a high volume of residual chlorine is produced, alkaline water with high pH is produced accordingly. For example, when water before electrolysis is neutral and pH and residual chlorine concentration of acidic water are 2.5 and 200 ppm, respectively, pH of alkaline water surpasses 11.9. In this manner, a pH shift in alkaline water becomes larger as corresponding to an amount of the chloride anion involved in the formation of residual chlorine.

Figure 2:
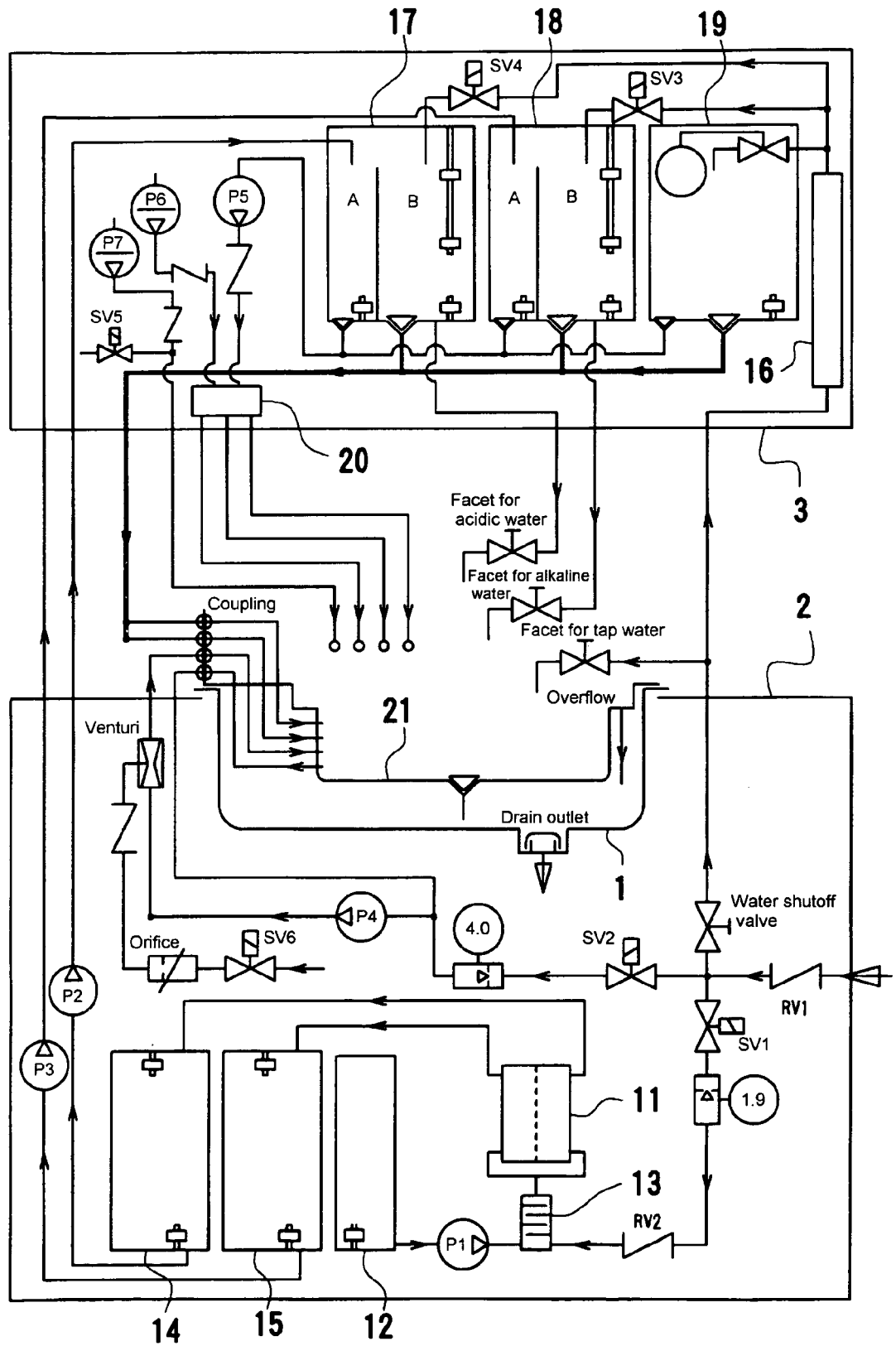
FIG. 2 is a block diagram illustrating a first modified Example in a method of cleaning an endoscope and a washing machine for endoscope shown in FIG. 1.

As shown in FIG. 2, the cleaning vessel 21 may be detachable with a sink 1 configured at a medical institution and the like. In this case, it can be detached to use as a sink when not used in cleaning of an endoscope. Even when the cleaning vessel 21 is detached, acidic water and alkaline water can be used for antibacterial cleaning, cleaning of fats and proteins and the like. They can also be used for preliminary cleaning of an endoscope. When the cleaning vessel 21 is attached to the sink 1, water overflowed from the cleaning vessel 21 can be discharged from the sink 1 so that acidic water, alkaline water or water for dilution can be circulated to clean an endoscope while overflowing from the cleaning vessel 21. A structure of the cleaning vessel 21 can be simplified such that the cleaning vessel 21 has no movable part except the drain valve 21a, which can open and close in conjunction with a drain valve of the sink, thereby facilitating handling and storage when detached from the sink 1 and enabling to reduce a manufacturing cost. The electrolytic cell 11, the electrolyte tank 12, the tank for alkaline water 15, the tank for acidic water 14 and the like may be accommodated in a storage space 2 under the sink 1 while the tank of diluting acidic water 17, the tank of diluting alkaline water 18, the tank for tap water 19, the water feed section for dilution 16 and the like may be accommodated in a wall cabinet 3 above the sink.

As shown in FIG. 2, each of the tank of diluting acidic water 17 and the tank of diluting alkaline water 18 may be composed of two tanks of a tank A and a tank B, so that acidic water fed from the tank for acidic water 14 or alkaline water fed from the tank for alkaline water 15 is flowed into the tank A, acidic water or alkaline water overflowed from the tank A is flowed into the tank B and water for dilution fed from the water feed section for dilution 16 to the tank B may be used to adjust to diluted acidic water or diluted alkaline water in the inside of the tank B. In this case, cleaning is conducted by feeding concentrated acidic water or alkaline water in the tank A through each of the couplings for channel cleaning water 20b into the inside of an endoscope channel while feeding diluted acidic water or diluted alkaline water in the tank B into the inside of the cleaning vessel 21 for cleaning.

As shown in FIG. 2, air pumps P5 and P6 may further be provided. In this case, after cleaning of the inside of an endoscope channel with alkaline water or acidic water is completed, the air pumps P5 and P6 can be driven to blow air into the channel inside to completely drain alkaline water or acidic water from the channel inside.

Figure 3:
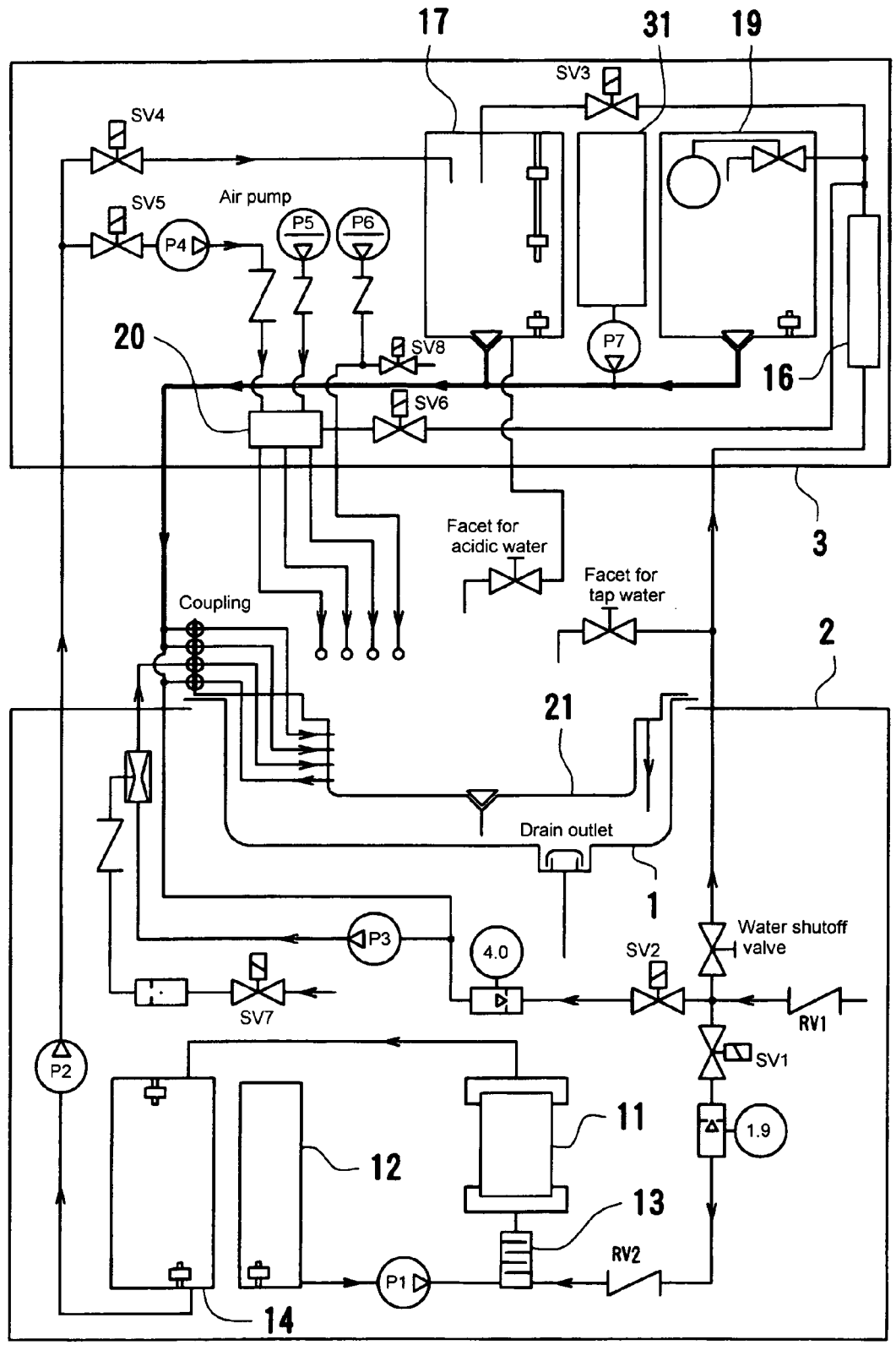
FIG. 3 is a block diagram illustrating a second modified Example in a method of cleaning an endoscope and a washing machine for endoscope shown in FIG. 1.

As shown in FIG. 3, the electrolytic cell 11 may be composed of an electrolytic cell without diaphragm and an electrolyte solution in the electrolyte tank 12 may be composed of a mixed aqueous solution of sodium chloride and an acid such as hydrochloric acid. In this case, acidic water with pH of 2 to 5 and residual chlorine concentration of 50 to 300 ppm can be produced in the electrolytic cell without diaphragm. As shown in FIG. 3, a tank for cleaning water 31, in which a detergent solution is stored may also be provided. In this case, there is no cleaning process with alkaline water but only those with water for dilution and acidic water, but when cleaning with water for dilution, the detergent is fed from the tank for cleaning water 31 to enhance a cleaning effect.

In the electrolytic cell 11 composed of the electrolytic cell without diaphragm, when brine and the like is directly electrolyzed, a weak alkaline aqueous solution of sodium hypochlorite is produced. There is a problem, in which this aqueous solution of sodium hypochlorite reacts with an organic substance to produce a hazardous trihalomethane since it is weakly alkaline. There is also a problem, in which tenfold or more of residual chlorine concentration is required to yield a similar level of sterilizing and oxidative effect, since residual chlorine in sodium hypochlorite is mostly a hypochlorite ion paired with a sodium ion, weak in activity as compared with a state of hypochlorous acid in an acidic region and as slow as one tenth to one hundredth in the reaction rate. To prevent such problems, hydrochloric acid and the like can be added to brine to acidify water in advance, which is electrolyzed to produce an acidic aqueous solution of hypochlorous acid in a state, in which residual chlorine is hypochlorous acid without generating a trihalomethane in the reaction with an organic substance.

Figure 4:
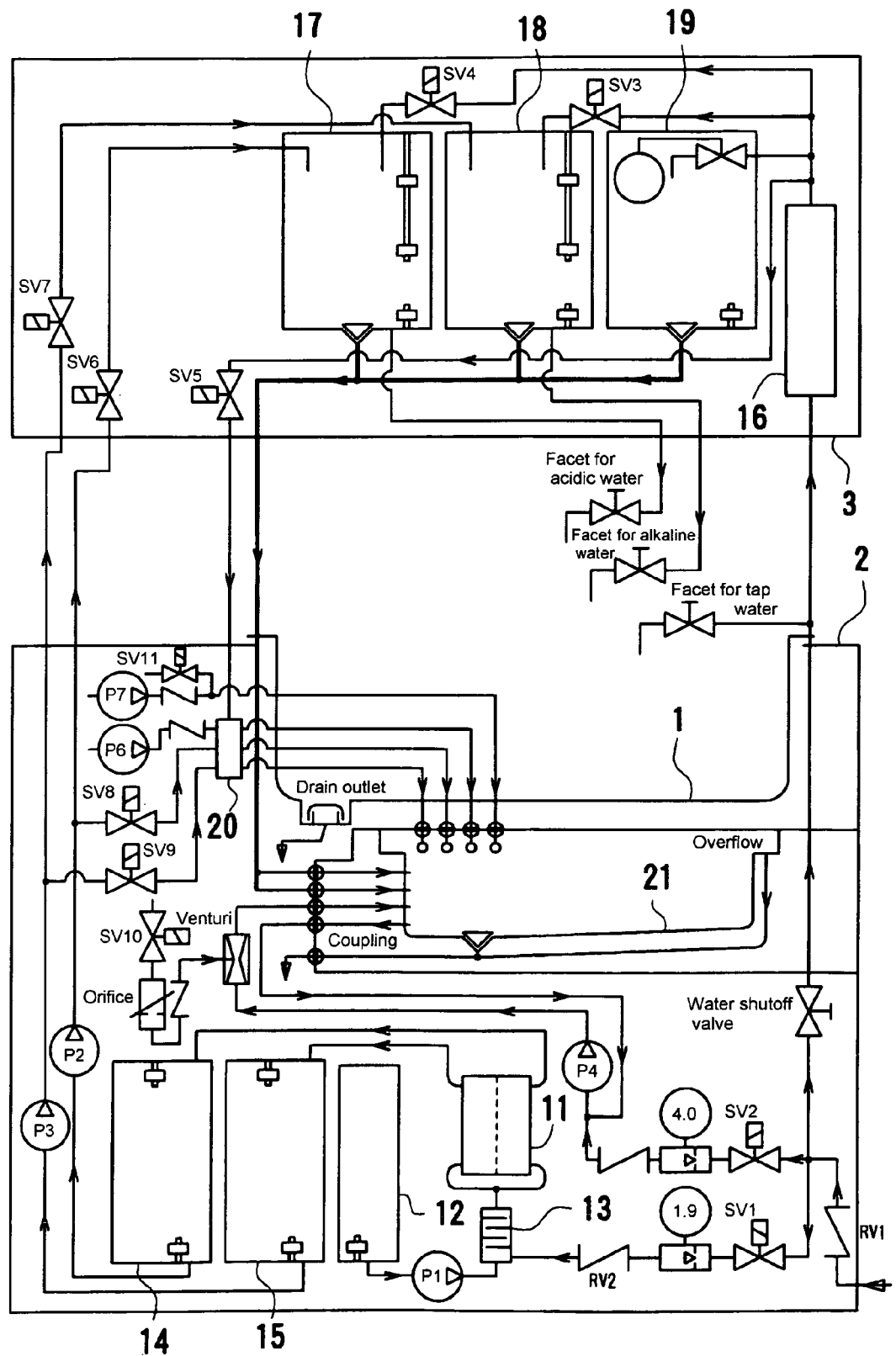
FIG. 4 is a block diagram illustrating a third modified Example in a method of cleaning an endoscope and a washing machine for endoscope shown in FIG. 1.

As shown in FIG. 4, the cleaning vessel 21 may be configured in the storage space 2 under the sink 1 installed in a medical institution and the like, so as to be pulled out from the storage space 2. In this case, when cleaning an endoscope, the cleaning vessel 21 can be pulled out from the storage space 2 under the sink 1 to place the endoscope in a given location of the cleaning vessel 21 to clean the endoscope. The cleaning vessel 21, which can be pulled out may be plurally configured in the storage space under the sink 1.

What is claimed is:

1. A method of cleaning an endoscope comprising:
producing undiluted acidic water,
adding water with pH higher than the acidic water to part of the undiluted acidic water to produce diluted acidic water having a pH higher than the undiluted acidic water,
contacting the diluted acidic water with only an external surface of the endoscope to clean the external surface of the endoscope, and
feeding a remainder of the undiluted acidic water through a channel port of the endoscope to clean an inside of the endoscope channel, so as to not contact the external surface of the endoscope.

2. A method of cleaning an endoscope comprising:
producing undiluted acidic water with a pH of 2 to 5 and a residual chlorine concentration of 50 to 300 ppm,
adding water with a pH of 6 or higher to part of the undiluted acidic water to produce diluted acidic water with a pH of 2.3 to 5.7 and a residual chlorine concentration of 10 to 60 ppm,
contacting the diluted acidic water with only an external surface of the endoscope to clean the external surface of the endoscope, and
feeding a remainder of the undiluted acidic water through a channel port of the endoscope, to clean the inside of the endoscope channel, so as to not contact the external surface of the endoscope.

* * * * *